(12) United States Patent (10) Patent No.: US 8,717,013 B2
Rohmann (45) Date of Patent: May 6, 2014

(54) DEVICE FOR DETECTING DAMAGE OF A TEST SPECIMEN MADE OF FERROMAGNETIC MATERIAL

(76) Inventor: Juergen Rohmann, Battenberg (DE)

(*) Notice: Subject to any disclaimer, the term of this patent is extended or adjusted under 35 U.S.C. 154(b) by 524 days.

(21) Appl. No.: 13/000,135

(22) PCT Filed: Mar. 19, 2009

(86) PCT No.: PCT/DE2009/000384
§ 371 (c)(1),
(2), (4) Date: Dec. 20, 2010

(87) PCT Pub. No.: WO2009/152788
PCT Pub. Date: Dec. 23, 2009

(65) Prior Publication Data
US 2011/0148406 A1 Jun. 23, 2011

(30) Foreign Application Priority Data
Jun. 21, 2008 (DE) .......................... 10 2008 029 525

(51) Int. Cl.
*G01N 27/82* (2006.01)
(52) U.S. Cl.
USPC .......................... 324/240; 324/242; 324/243

(58) Field of Classification Search
USPC .......................................... 324/240, 242, 243
See application file for complete search history.

(56) References Cited

U.S. PATENT DOCUMENTS 3,535,624 A * 10/1970 Wood ............................ 324/226
5,128,613 A * 7/1992 Takahashi ..................... 324/235

* cited by examiner

*Primary Examiner* — Reena Aurora
(74) *Attorney, Agent, or Firm* — Galgano & Associates, PLLC; Thomas M. Galgano; Jessica G. Bower

(57) ABSTRACT

The device comprises a magnetization unit, which generates a constant magnetic field, to which the test specimen (12) is exposed so as to magnetize it. The magnetization unit and test specimen (12) carry out a relative motion to each other, thereby inducing eddy currents in the test specimen (12). The magnetization unit has at least one yoke (10) projecting in the direction of the relative motion. In addition to a probe (14), which is offset toward the back with respect to the magnetization unit in the direction of the relative motion and which is suited to detect damage based on the influence of the damage on the induced eddy current, the device comprises at least one further probe (16) between the yoke limbs of the magnetization unit.

17 Claims, 2 Drawing Sheets

DEVICE FOR DETECTING DAMAGE OF A TEST SPECIMEN MADE OF FERROMAGNETIC MATERIAL

The invention relates to a device for detecting manufacture-related or operation-related damage sites in a test specimen made of ferromagnetic material, the device having a magnetization unit, which generates a constant magnetic field, to which the test specimen is exposed in order to magnetize it, wherein the magnetization unit and test specimen move relative to one another, thus inducing eddy currents in the test specimen, and wherein the magnetization unit has at least one yoke with width in the direction of the relative motion, and the device also having a sensor set back from the magnetization unit in the direction of the relative motion, which sensor is suitable for detecting defect sites on the basis of its influence on the induced eddy currents.

Such a device is known from DE 102004045271 A1. The device is provided especially but not exclusively for testing of laid railroad rails.

Railroad rails are subjected during on-going operation to material fatigue and wear, which lead to development of typical damage sites. Squats and head checks may be mentioned as examples. Squats are two-dimensional separations lying under the top surface of the rail and oriented mainly parallel to the surface. Head checks are transversely oriented cracks in the zone of the running edge and occur mainly along the curves on the outer rail. In addition, railroad rails may have dent-like damage sites, caused by slipping of the wheels during starting or braking.

Material damage sites in railroad rails may have damage depths of several mm. In an automated test sequence, the objective is to detect the damage sites, to locate them exactly and to assess their danger potential, and so great importance is attached to quantitative measurement of the damage depth.

To test railroad rails, a rail-mounted vehicle transporting the test device travels over them. The target parameters are a traveling velocity of several kilometers if not one hundred kilometers per hour and faster, a damage-detection depth of several mm and sufficiently accurate location of the damage that repeated detection of any damage can be guaranteed.

The device according to DE 102004045271 A1 is suitable for detecting damage sites of great depth, locating them accurately and quantitatively measuring their depth, all at high relative velocity between the test specimen and the magnetization device.

The object of the invention is to measure the nature, location and severity of damage sites even more accurately with a device of the class mentioned in the introduction.

In the device that achieves this object, at least one sensor, suitable for measuring the induced eddy currents and/or the magnetic leakage flux, is preferably disposed centrally between the arms of the yoke of the magnetization device.

In a preferred embodiment, the device has at least one further sensor, which is set ahead of the magnetization device in the direction of relative motion and is suitable for measuring induced eddy currents and/or the magnetic leakage flux. Preferably this sensor is disposed ahead of the front arm of the yoke of the magnetization device.

Experiments have shown that the significance of damage detection may be improved by measuring the eddy currents and/or the magnetic leakage flux not only in the decaying magnetic trailing field but additionally in the magnetization and preferably also ahead of the magnetization. By the detection of head checks in the magnetization and preferably also ahead of the magnetization, their damage depth can be determined with high accuracy. This is of great practical importance, since it is economically worthwhile to grind out head checks of small damage depth.

In a preferred embodiment, the width (extent from pole to pole) of the yoke of the magnetization device in the direction of relative motion is all the much greater the higher the relative velocity and the greater the desired detection depth.

In a preferred embodiment, the magnetization intensity of the magnetization device can be regulated. Thus the magnetization intensity can be adapted to the desired damage-detection depth and the magnitude of the relative velocity between the magnetization device and the test specimen. The magnetization depth should be all the greater the higher the relative velocity and the greater the desired detection depth.

The magnetization device may be a permanent magnet or an electromagnet. Regulation of the magnetization intensity may be achieved mechanically or electrically.

In a preferred embodiment, the sensor(s) is or are a Hall-effect detector, a magnetic-field-sensitive semiconductor or a SQUID.

In a preferred embodiment, the sensor(s) is or are one or more sensor(s) operating according to the magnetic induction technique for eddy-current testing of materials.

The inventive device has a preferred use for testing a laid railroad rail. For this purpose, as illustrated in FIG. 3, it is disposed on a rail-mounted vehicle traveling over the rail to be tested at a speed causing induction of eddy currents.

The inventive device has a further preferred use for testing rotationally symmetric test specimens. Conceivable specimens are wheels, especially railroad wheels, round bars, tubes and other round material in solid or hollow form. During the test, the device and the test specimen rotate relative to one another in a manner that induces eddy currents. Preferably the device is stationary during the test, while the test specimen is driven in rotation around a central axis.

The invention will be explained in more detail hereinafter with reference to the drawings, wherein.

Figure 1:
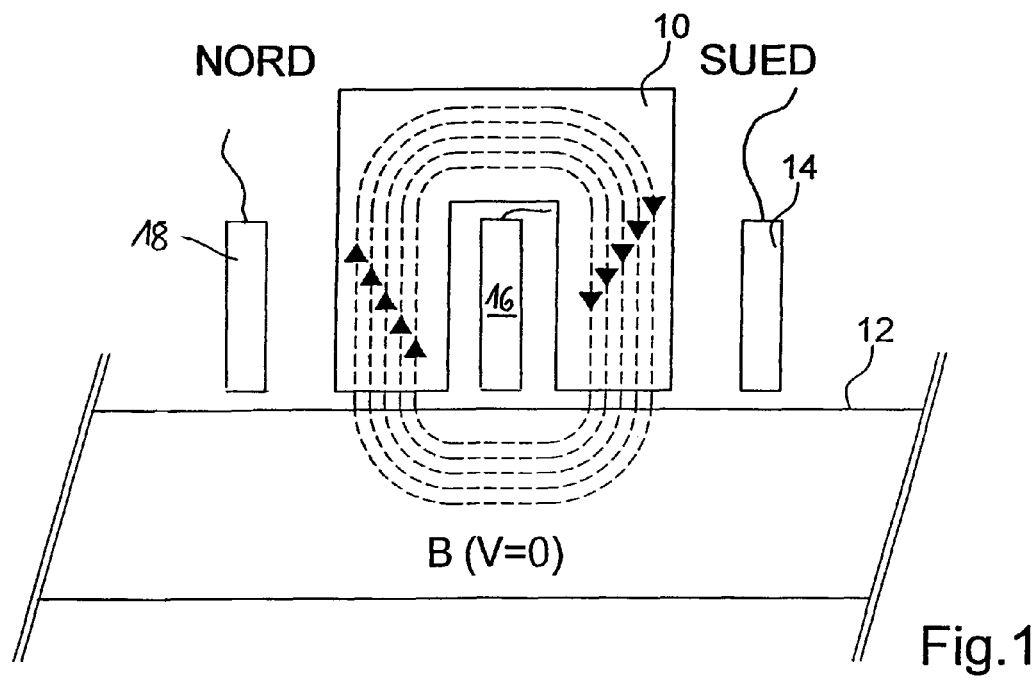
FIG. 1 shows a schematic side view of a test specimen and a magnetization device at rest, or in other words when the relative velocity is zero.
Figure 2:
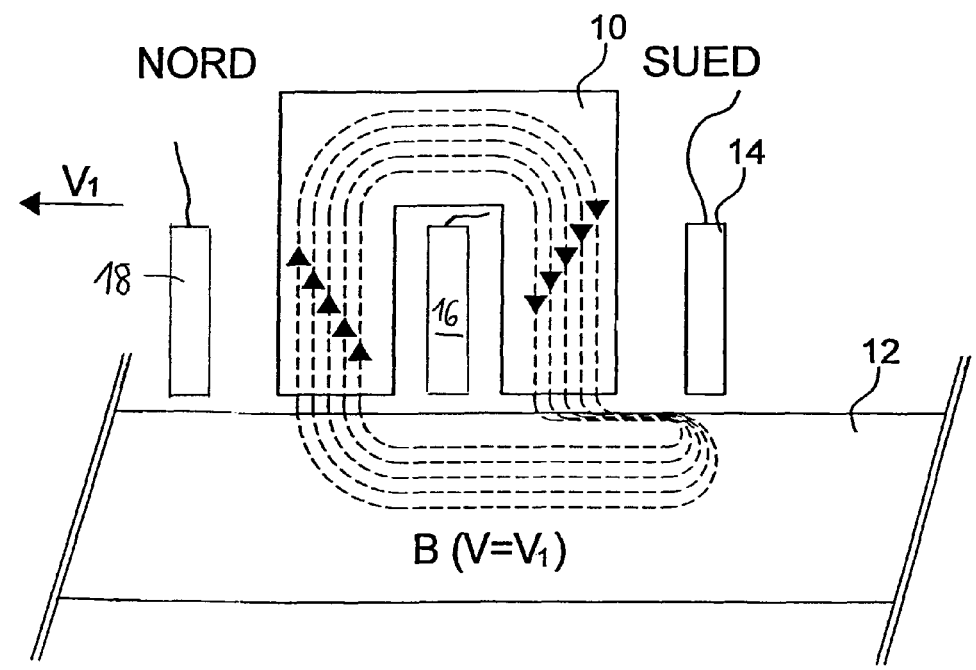
FIG. 2 shows the same view when the relative velocity $v_1$ is non-zero.
Figure 3:
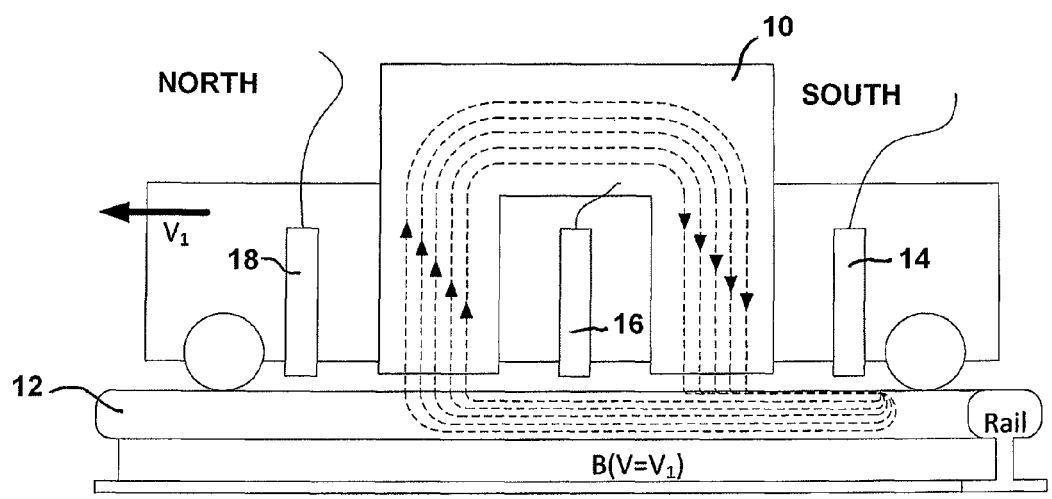
FIG. 3 shows the device disposed on a rail-mounted vehicle traveling over a rail when the relative velocity $v_1$ is non-zero.

FIGS. 1 and 2 show yoke 10 of a magnetization device, which generates a constant magnetic field B. A test specimen 12, via which the magnetic circuit is closed, is disposed ahead of yoke 10 and separated therefrom by an air gap.

FIG. 1 shows the magnetic field pattern when test specimen 12 and the magnetization device are at rest, or in other words when the relative velocity v is equal to zero. FIG. 2 shows the field pattern for a non-zero relative velocity $v_1$. A magnetic braking field (trailing field), in the region of which eddy currents are induced, is developed at a position set back in the direction of motion. This phenomenon in known from the eddy-current brake.

The eddy currents induced by the relative motion are used to detect damage sites in test specimen 12. The damage sites have an influence on the eddy currents, and this influence can be measured with a sensor 14 set back from the magnetization device in the direction of motion.

A second sensor 16 is disposed centrally between the arms of the yoke of the magnetization device, and a third sensor 18 is disposed ahead of the front arm of the yoke of the magnetization device in the direction of relative motion.

LIST OF REFERENCE NUMERALS

10 Yoke
12 Test specimen

14 Sensor
16 Sensor
18 Sensor

The invention claimed is:

1. A method of use of a device for detecting manufacture-related or operation-related damage sites in a test specimen made of ferromagnetic material, comprising the steps of:
providing a test specimen made of ferromagnetic material;
providing a device for detecting manufacture-related or operational-related damage sites in said test specimen, comprising a magnetization unit, which generates a constant magnetic field, wherein said magnetization unit has at least one yoke with width in the direction of a relative motion, said yoke having arms; a first sensor set back from said magnetization unit in the direction of relative motion, which first sensor detects defect sites on the basis of the influence of said defect sites on induced eddy currents; at least one second sensor, for measuring at least one member selected from the group consisting of induced eddy currents and magnetic leakage flux, disposed between said arms of said yoke of said magnetization unit; and at least one third sensor, which is set ahead of said magnetization unit in the direction of relative motion, for measuring at least one member selected from the group consisting of induced eddy currents and magnetic leakage flux;
exposing said test specimen to said magnetic field generated by said magnetization unit in order to magnetize said test specimen;
moving said magnetization unit and said test specimen relative to one another to induce eddy currents in said test specimen;
utilizing said at least one second sensor to measure at least one member selected from the group consisting of the induced eddy currents and magnetic leakage flux;
utilizing said at least one third sensor to measure at least one member selected from the group consisting of the induced eddy currents and magnetic leakage flux; and
utilizing said first sensor to detect defect sites in said test specimen, based on the influence of said defect sites on the induced eddy currents.

2. The method according to claim 1, wherein:
said second sensor is disposed centrally between said arms of said yoke.

3. The method according to claim 2, wherein:
one of said arms of said yoke is a front arm in the direction of relative motion and said third sensor is disposed ahead of said front arm of said yoke of said magnetization unit.

4. The method according to claim 1, wherein:
said width of said yoke in the direction of relative motion is all the much greater the higher the relative velocity and the greater the desired detection depth.

5. The method according to claim 1, wherein:
the magnetization intensity of said magnetization unit can be regulated.

6. The method according to claim 1, wherein:
said magnetization unit is a permanent magnet.

7. The method according to claim 1, wherein:
said magnetization unit is an electromagnet.

8. The method according to claim 1, wherein:
said first sensor is a member selected from the group consisting of a Hall-effect detector, a magnetic-field-sensitive semiconductor, and a SQUID.

9. The method according to claim 1, wherein:
said first sensor operates according to the magnetic induction technique for eddy-current testing of materials.

10. The method according to claim 1, wherein:
said second sensor is a member selected from the group consisting of a Hall-effect detector, a magnetic-field-sensitive semiconductor, and a SQUID.

11. The method according to claim 1, wherein:
said third sensor is a member selected from the group consisting of a Hall-effect detector, a magnetic-field-sensitive semiconductor, and a SQUID.

12. The method according to claim 1, wherein:
said second sensor operates according to the magnetic induction technique for eddy-current testing of materials.

13. The method according to claim 1, wherein:
said third sensor operates according to the magnetic induction technique for eddy-current testing of materials.

14. A method of use of a device for testing a laid railroad rail, comprising the steps of:
providing a laid railroad rail made of ferromagnetic material;
providing a device for detecting manufacture-related or operation-related damage sites in said railroad rail, comprising a magnetization unit, which generates a constant magnetic field, wherein said magnetization unit has at least one yoke with width in the direction of a relative motion, said yoke having arms; a first sensor set back from said magnetization unit in the direction of said relative motion, which first sensor detects defect sites on the basis of the influence of said defect sites on induced eddy currents; at least one second sensor, for measuring at least one member selected from the group consisting of induced eddy currents and magnetic leakage flux, disposed between said arms of said yoke of said magnetization unit; and at least one third sensor, which is set ahead of said magnetization unit in the direction of relative motion, for measuring at least one member selected from the group consisting of induced eddy currents and magnetic leakage flux;
disposing said device on a rail-mounted vehicle traveling over said rail to be tested;
exposing said rail to said magnetic field generated by said magnetization unit in order to magnetize said rail;
moving said rail-mounted vehicle over said rail at a velocity causing induction of eddy currents in said rail;
utilizing said at least one second sensor to measure at least one member selected from the group consisting of the induced eddy currents and magnetic leakage flux;
utilizing said at least one third sensor to measure at least one member selected from the group consisting of the induced eddy currents and magnetic leakage flux; and
utilizing said first sensor to detect defect sites in said rail, based on the influence of said defect sites on the induced eddy currents.

15. A method of use of a device for testing a rotationally symmetric test specimen, comprising the steps of:
providing a test specimen made of ferromagnetic material;
providing a device for detecting manufacture-related or operation-related damage sites in said test specimen, comprising a magnetization unit, which generates a constant magnetic field, wherein said magnetization unit has at least one yoke with width in the direction of a relative motion, said yoke having arms; a first sensor set back from said magnetization unit in the direction of said relative motion, which first sensor detects defect sites on the basis of the influence of said defect sites on induced eddy currents; at least one second sensor, for measuring at least one member selected from the group consisting of induced eddy currents and magnetic leakage flux, disposed between said arms of said yoke of said magnetization unit; and at least one third sensor, which is set ahead of said magnetization unit in the direction of relative motion, for measuring at least one member selected from the group consisting of induced eddy currents and magnetic leakage flux;

exposing said test specimen to said magnetic field generated by said magnetization unit in order to magnetize said test specimen;

rotating said device and said test specimen relative to one another in a manner that induces eddy currents in said test specimen;

utilizing said at least one second sensor to measure at least one member selected from the group consisting of the induced eddy currents and magnetic leakage flux;

utilizing said at least one third sensor to measure at least one member selected from the group consisting of the induced eddy currents and magnetic leakage flux; and utilizing said first sensor to detect defect sites in said test specimen, based on the influence of said defect sites on the induced eddy currents.

16. The method according to claim 15, wherein:
said device is stationary, while said test specimen is driven in rotation around a central axis.

17. The method according to claim 15, wherein:
said test specimen is a member selected from the group consisting of a wheel, a round bar and a tube.

* * * * *